United States Patent

Butcher et al.

[11] Patent Number: 6,004,300
[45] Date of Patent: Dec. 21, 1999

[54] COMPOSITE HYPODERMIC SYRINGE PISTON

[76] Inventors: Robert M Butcher, 511 Emmas Grove Rd., Fletcher, N.C. 28732; Sherman M. Brod; Sandra Crane Brod, both of 403A S. Willow, Tampa, Fla. 33606

[21] Appl. No.: 08/964,161

[22] Filed: Nov. 4, 1997

Related U.S. Application Data

[63] Continuation-in-part of application No. 08/919,680, Aug. 28, 1997.

[51] Int. Cl.[6] ............................................. A61M 5/315
[52] U.S. Cl. .................................... 604/222; 604/218
[58] Field of Search ......................... 604/82, 89–92, 604/218, 222, 230

[56] References Cited

U.S. PATENT DOCUMENTS

| | | | |
|---|---|---|---|
| 4,385,025 | 5/1983 | Salerno et al. | |
| 4,997,423 | 3/1991 | Okuda et al. | 604/230 |
| 5,411,488 | 5/1995 | Pagay et al. | 604/218 |
| 5,578,011 | 11/1996 | Shaw | 604/110 |
| 5,735,825 | 4/1998 | Stevens et al. | 604/218 |
| 5,769,822 | 6/1998 | McGary et al. | 604/110 |

*Primary Examiner*—Corrine McDermott
*Attorney, Agent, or Firm*—Pendorf & Cutliff

[57] ABSTRACT

A process for forming a composite piston of at least two materials, preferably a rigid material and an elastic material, the materials being chemically fused in a modular mold, and the plunger formed thereby. The process comprising injection molding one of the rigid material and elastic material in a mold to form a first piston part; forming a cavity in the mold adjacent the first piston part; injection molding the other of the rigid material and plastic material in the cavity to form a second piston part in contact with the first piston part; and removing the piston having a rigid part and an elastic part from said mold. Upon opening of the mold, complete, finished pistons are presented. The material for forming the elastic part preferably includes a lubricant. The process reduces assembly costs, quality control concerns, and contamination due to human contact.

14 Claims, 4 Drawing Sheets

COMPOSITE HYPODERMIC SYRINGE PISTON

Related U.S. Application

This application is a continuation-in-part of U.S. application Ser. No. 08/919,680, filed Aug. 28, 1997.

BACKGROUND OF THE INVENTION

1. Field of the Invention

This invention relates to a modular molding process for forming a composite piston for a hypodermic syringe wherein thermoplastic rubber and plastic parts of the piston are integrally formed in the same mold in a multi-phase, or modular, injection molding process, and wherein the composite piston is thereafter ready to be seated on the piston end of a conventionally made syringe shaft.

2. Description of the Related Art

Hypodermic syringes are comprised of a barrel, which receives a fluid to be injected, and a plunger, which transmits force via a piston rod to a piston for either drawing in or dispensing the fluid. The plunger is conventionally comprised of a rigid plastic thumb press, a flexible rubber piston for sealingly engaging the walls of the barrel, and a shaft for transmission of force between the thumb press and piston. Conventionally, plungers are constructed in three separate steps: a step of manufacturing a rigid plunger shaft, a step of manufacturing an elastic rubber piston, and a step of assembling the rubber piston onto the rigid plunger shaft using a variety of techniques including mechanical interlock, adhesive, ultrasonic welding, heat fusion or the like.

The pistons are conventionally comprised wholly of a resilient, thermoplastically processable rubber mixture, consisting predominantly of a block polymer, and can contain a quantity of a polyolefin. Such a composition is necessary to provide good resilience, while presenting minimal relaxation phenomenon in the course of use, thus insuring a fluid-tight seal between the piston and the inner surface of the syringe barrel. Further, such a composition is resistant to the most common medical agents. Unfortunately, such rubber mixtures are much more expensive, on a weight basis, than the materials used to construct the other portions of the syringe.

The rubber pistons are typically mass produced in at least four separate steps: a step of heat-impression stamping a rubber sheet around core pins, tumbling the rubber pistons to debur them, and to eliminate any flash created during the stamping process, washing the pistons to eliminate the dust and debris created in the tumbling process, and lubricating the finished piston.

In terms of time and efficiency, this multi-step piston-manufacturing process is costly and requires quality control. Further, when the rubber sheet is heat-impression stamped around core pins, latent variations in rubber density are created in the piston. These density variations may be attributed either to unavoidable folding of the rubber sheet around the core pins or to variations of density in the rubber sheet itself. These density variations (1) allow the plunger rods to pull out of the pistons thereby resulting in a 5–7% failure rate in the syringe and (2) interfere with the fluid-tightness of the seal between the piston and the syringe barrel, allowing failure in operation such as in an emergency room.

There is also a problem of balancing the softness properties of the rubber-if the rubber is too hard, the seal forming properties are impaired, and if the rubber is too soft, the piston will come unseated from the plunger shaft during drawing in of fluids. In a hospital emergency room, speed and reliability are a precious commodity. Accordingly, it is absolutely critical that hypodermic needles meet a high standard of reliability and performance, and any feature that will contribute to reliability of the syringe would be advantageous.

If these reliability considerations could be met, then it would be desirable to have a process for producing a syringe plunger piston with significantly lowered production costs.

SUMMARY OF THE INVENTION

The present inventors have contemplated the state of the art as discussed above and have devised a process for forming a composite piston for a hypodermic syringe wherein thermoplastic rubber and plastic parts of the plunger are integrally formed in the same mold in a multi-phase, or modular, injection molding process, and wherein the composite piston is thereafter ready to be seated on a conventionally made syringe shaft. Further, the composite piston of the present invention is interchangeable with the conventional, wholly rubber pistons and, therefore, may be substituted in place of rubber in the conventional piston-shaft assembly equipment.

By sequentially molding a composite piston according to the present invention, less rubber mixture is needed to produce each piston unit; hence, economy of materials is maximized and unit cost is lowered.

Further, by sequentially molding a composite piston according to the present invention, the faults in the rubber locking mechanism of the pistons, caused by the variations in rubber density are eliminated. The injection molded plastic locking mechanism is much more precise. Therefore, the failure rate of the connection of the piston to the plunger rod is reduced significantly.

Finally, by sequentially molding a composite piston according to the present invention, several production steps are eliminated: heat-impression stamping of rubber sheets, tumbling to eliminate flash and to debur, washing to eliminate the dust and debris caused by the tumbling, and lubricating the finished piston.

The inventors further considered that any article comprised of two or more materials must meet several requirements for successful employment as a syringe or syringe piston. Syringes must be sterile and debris-free in view of their intended use and must have special physical properties such as liquid tightness, inertness to medicaments, gas tightness, long storage life, and good sliding property. The inventors have invented a method for creating a two-material piston, where the materials may be integrated in a simple way or a complex way depending upon the needs of the designer, and where careful selection of the composite materials results in a chemical attachment within the mold. Each material is precisely formed into its respective component shape.

Whereas the conventional piston fits over the plunger shaft end like a sheath and is comprised of a single material (rubber), the plunger piston of the present invention has a bi-layer construction with a more rigid inner sheath and a comparatively flexible elastic outer sheath, yet the piston of the present invention has the same shape and dimensions as the conventional piston and thus can be used interchangeably therewith (e.g., in piston and shaft assembling machines). Specifically, the basic piston design includes a rigid material forming a piston infrastructure, designated the inner sheath. A substantially rigid biocompatible thermoplastic material, such as a polystyrene, or high-density polyethylene or polypropylene, is a preferred material for the inner sheath. The inner sheath includes an internal surface which defines an engagement cavity for receiving the plunger shaft end (similarly to the conventional all-rubber piston). It is for this reason that it is important that the inner sheath be made of a material that yields sufficiently to receive the plunger shaft end, yet is rigid enough to mechanically lock. It is an advantage of the present invention that, being made of rigid thermoplastic, the inner sheath establishes a rigid lock-on when the composite piston is seated upon the plunger shaft end, as compared to the more flexible lock-on created if the piston were completely composed of rubber. The more rigid lock-on is preferred over a flexible lock-on because a rigid lock-on ensures that the piston will not become unseated from the plunger shaft during drawing in of a fluid. The inner sheath further defines a conical apex for engaging with the bottom, or needle end, of the syringe barrel during full actuation of the syringe plunger. As explained above, the piston has an outer sheath, which is resilient and elastic, the function of which is to engage the inner wall of the syringe barrel with adequate pressure to create a fluid-tight seal for drawing and injecting a fluid. The outer sheath partially enshrouds the inner sheath, leaving the conical apex of the inner sheath exposed. An elastomeric material, preferably thermoplastic rubber (such as SANTOPRENE™, a product of Monsanto Company), or a thermoplastic elastomer having a long shelf life, such as vinyl acetate copolymer, are preferred materials for the outer sheath. In the case of thermoplastic elastomers, these materials are compatible with the thermoplastic resins in the sense that they fuse at areas of interface within a mold into which they are injected, even if they are sequentially injected rather than co-injected, to produce an effectively unitary or integral article. It should be understood that in accordance with the present invention it is preferred that the two materials be compatible (fuse). If non-fusing materials are used, it is preferred that the outer wall of the inner sheath be roughened, so that upon molding and curing rubber thereon the outer rubber sheath will mechanically lock onto this roughened surface.

The outer sheath further defines an upper rib seal and lower rib seal which contact the inner surface of the syringe barrel in order to maximize fluid-tightness property.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other mold assemblies for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a better understanding of the present invention, reference is made to the accompanying drawings, which are incorporated herein by reference and in which.

DETAILED DESCRIPTION OF THE INVENTION

Figure 1:
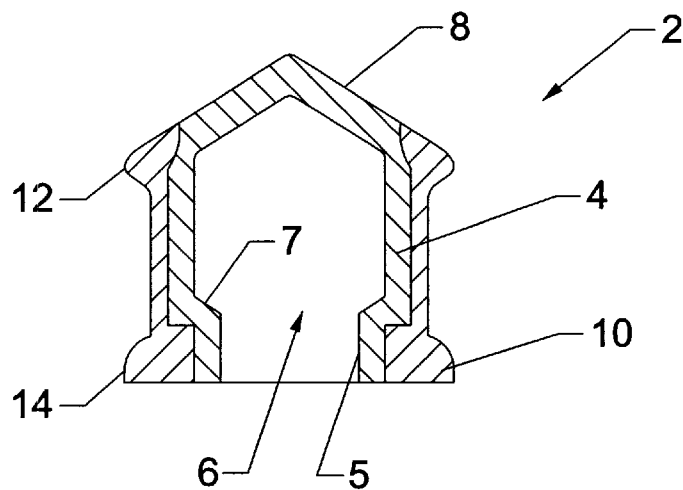
FIG. 1: sets forth a sectional view of the preferred embodiment of the composite plunger piston.

Two advantages, as well as two major distinguishing features, of the two-material (composite) piston of the present invention are (1) its reduced production cost and (2) reduced failure rate.

In accordance with the present invention, the piston is produced by injection molding, and therefore the conventional requirements to tumble and to clean the conventional compression molded pistons are eliminated. Further, the present invention permits the design and construction of unique pistons. Molding of complex features is accomplished by changing out modular mold parts, or by moving mold parts between first and second positions (see U.S. Pat. No. 4,385,025, the disclosure of which is incorporated herein by reference), or by a combination of the above.

Along the same vein as U.S. Pat. No. 4,385,025, U.S. Pat. No. 5,366,805 teaches integral moldings in which thermosetting resin, especially polycarbonate resin, and silicone rubber are firmly united or bonded together to form one article. The process involves injection molding a polycarbonate resin into a preform sheet, rotating half of the mold 180 degrees about a horizontal axis in order to define a cavity for molding a silicone rubber sheet between the exposed surface of the resin sheet and the existing recess, injection molding the silicone rubber so that it contacts a surface of the preform, and curing the silicone rubber. While this principle may be used to construct parts of the plunger piston according to the present invention, the problem of seams, described above, remains a problem to be solved by the present invention.

As in U.S. Pat. No. 4,385,025, the term "substantially rigid thermoplastic material" (sometimes shortened hereafter to "thermoplastic" for brevity) herein means a solid substantially rigid material which has the property of melting (softening to the point of becoming a liquid) when heated to a suitable temperature and of hardening and becoming a solid and substantially rigid again when cooled to room temperature, i.e., 70° F., and the term "thermoplastic elastomer" (sometimes shortened hereafter to "elastomer"

for brevity) means a solid material which has the property of melting when heated to a suitable temperature and of hardening and becoming a solid which is resilient and shape retentive and behaves as an elastomer when cooled to room temperature, such as a thermoplastic rubber. These thermoplastic materials may consist of a single thermoplastic polymer substance or a mixture of such substances, with or without additives such as colorants, plasticizers, antioxidants, stabilizers, and other functional ingredients that suitably modify one or more of the physical properties of the thermoplastic substance(s).

As previously mentioned, one example of a thermoplastic rubber that would serve as an "elastomer" is SANTOPRENE™, which is considered a thermoplastic alloy. SANTOPRENE™ is essentially a thermoplastic polypropylene gel, infused with a dense matrix of microscopic particles of vulcanized rubber. The rubber particles are typically about one micrometer in diameter.

A method for obtaining a thermoplastic rubber for diverse industrial applications, by blending processed rubber materials to a thermoplastic, is disclosed in U.S. Pat. No. 5,359,007 (Oliveira Da Cunha Lima), issued Oct. 25, 1994, the disclosure of which is incorporated herein by reference. In essence, raw materials which include used rubber artifacts, like tires and other rubber products, are devulcanized by means of physical, chemical, or physico-chemical processes, transformed into a uniform and regular batch, which is blended to a thermoplastic, thus obtaining a thermoplastic rubber. Further, the use of thermoplastic rubber in medical products is disclosed in "Kraton Thermoplastic Rubber Medical Products", by Shell Chemical Co., Technical Bulletin SC:1032-88 (1988), the disclosure of which is incorporated herein by reference.

It is known to mix lubricant components into the rubber mixture of the syringe piston, prior to piston formation, in order to reduce friction and thus lower the forces required to move the rubber piston along the barrel. Such lubricant components may be used with the present invention as well. For example, to improve the sliding characteristics of the piston, the rubber mixture can contain a quantity of 0.1 to 2 wt % of a silicone rubber. The improved sliding characteristics eliminate stick-slip effects. Operation of the syringe is simplified, and the medicinal agent can be administered in accurately predetermined doses.

The preferred embodiments and method of the invention will now be described with reference to the figures. The terms "upper" and "lower" are used herein only with reference to the figures, and it will be understood that the mold is not limited to the orientation shown in the figures and may be vertical, horizontal, or in any other orientation.

It should also be understood that certain features of the pistons, such as piston rib seals, have been exaggerated in the figures for illustrative purposes, and that the pistons can assume a wide variety of shapes and designs for use in any field. In the medical field, syringes for injection or evacuation take a wide variety of shapes and sizes, and are typically from 0.1 to 1000 cc, more typically from 0.5 cc capacity to 500 cc capacity.

Figure 2:
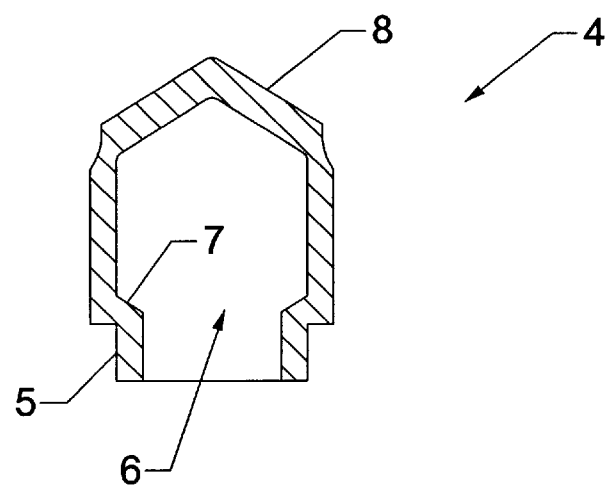
FIG. 2: sets forth a sectional view of the piston inner sheath, in isolation.
Figure 9:
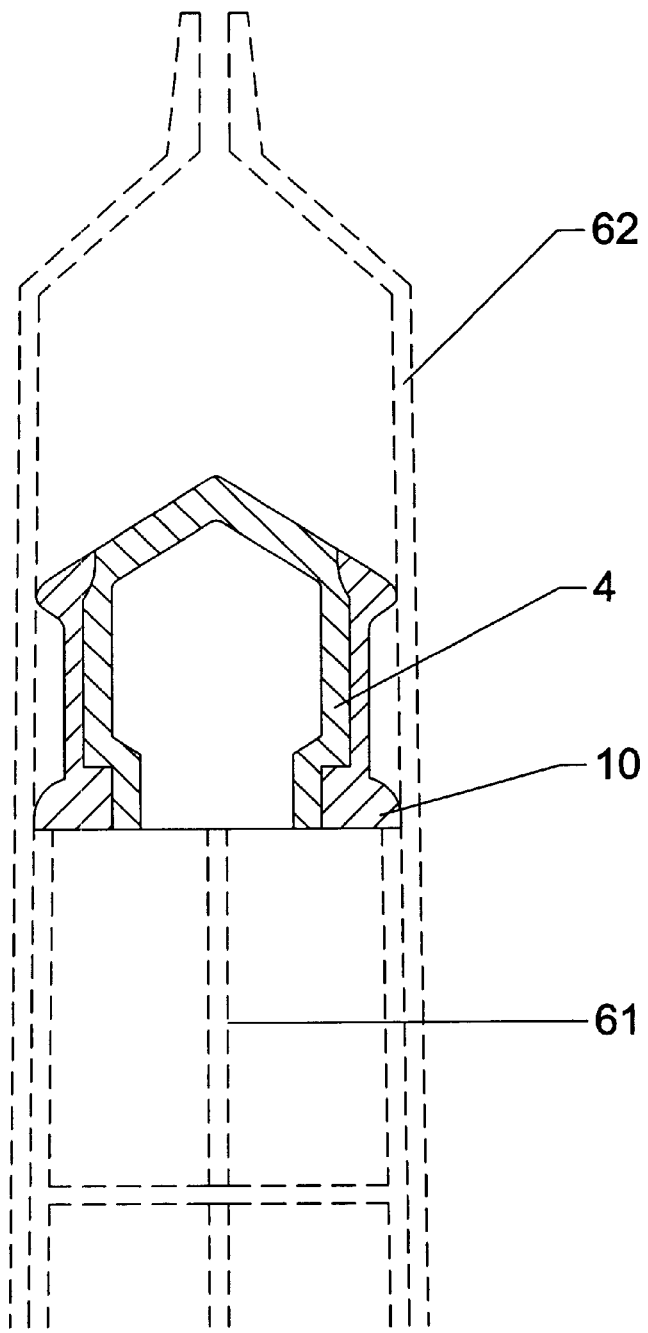
FIG. 9 shows the piston of the invention seated on a conventional shaft and located within a barrel of a conventional hypodermic syringe.

Referring now to FIG. 1, the plunger piston 2 of the present invention includes a two-material bi-layer. Specifically, the basic piston design includes a rigid material forming a piston infrastructure, or inner sheath 4, as shown sectionally in FIG. 1, and in isolation in FIG. 2. A substantially rigid biocompatible thermoplastic material, such as a polystyrene, or high-density polyethylene or polypropylene, is a preferred material for the inner sheath. The inner sheath 4 has an internal surface that defines an engagement cavity 6 for receiving the plunger shaft end (not shown). The inner sheath 4 further defines a tapering conical apex 8 for engaging with the bottom of the syringe barrel (not shown) during full actuation of the syringe plunger (not shown). The inner sheath 4 also has a mechanical locking collar 5, which is narrower of diameter than the rest of the inner sheath. The collar 5 functions to reliably secure the composite piston upon a plunger shaft-end to ensure that the piston does not become unseated from the plunger shaft (not shown). It is preferable that the intersection between the engagement cavity 6 and the collar 5 describe a taper 7, as shown in FIGS. 1 and 2. It is further preferable that the taper 7 have an angle advantageous to both liberating the completed piston 2 from the mold and also to retention of the piston 2 upon the plunger shaft 61 (shown in broken lines in FIG. 9). To this end, the angle of the taper 7 is preferably from 2–4°. In one alternative embodiment, the inner walls of the collar 5 may be bowed slightly inward, in a convex fashion, to facilitate liberation of the finished plunger 2 from the mold and retention of the piston 2 upon the plunger shaft 61 (shown in broken lines in FIG. 9).

Further, the piston 2 has an outer sheath 10, the function of which is to engage the inner wall of the syringe barrel 62 (shown in broken lines in FIG. 9) with adequate pressure to create a fluid-tight seal for drawing and injecting a fluid. As shown sectionally in FIG. 1 and in isolation in FIG. 3, the outer sheath 10 partially enshrouds the inner sheath 4, leaving the conical apex 8 of the inner sheath 4 exposed. An elastomeric material, preferably thermoplastic rubber (such as SANTOPRENE™, a product of Monsanto Company), or a thermoplastic elastomer having a long shelf life, such as vinyl acetate copolymer, are preferred materials for the outer sheath 10. In the case of thermoplastic elastomers, these materials are compatible with the thermoplastic resins in the sense that they fuse at areas of interface within a mold into which they are injected, even if they are sequentially injected rather than co-injected, to produce an effectively unitary or integral article. It should be understood that in accordance with the present invention it is preferred that the two materials be compatible so that they fuse. If the two materials are non-compatible, the piston outer sheath 10 and piston inner sheath 4 should be mechanically interconnected.

Figure 3:
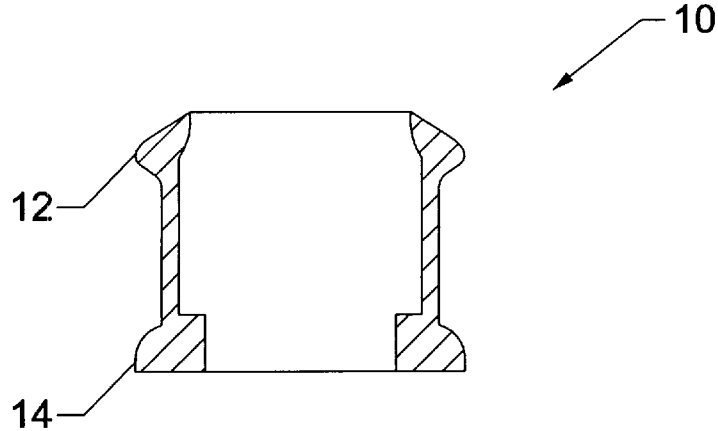
FIG. 3: sets forth a sectional view of the piston outer sheath, in isolation.

As shown in FIGS. 1 and 3, the outer sheath 10 further defines an upper rib seal 12 and lower rib seal 14 which extend radially outward from the outer sheath 10 to sealingly contact the inner surface of the syringe barrel (not shown) in order to maximize fluid-tightness property.

Though not specifically expressed in the drawings, it has been contemplated by the inventors to have variations in the thickness of the inner sheath 4 and outer sheath 10. For example, in an alternative embodiment, the area of the rigid inner sheath 4 which lies beneath the upper rib seal 12 may be thinner to allow for an upper rib seal 12 with a thickness which approaches the thickness of the lower rib seal 14. By "thinning out" the rigid material beneath the upper rib seal 12, the upper rib seal 12 may be thicker, thus permitting greater compressibility while liberating the finished piston 2 from the mold.

The materials can be considered "fusion-compatible" if both materials are non-polar or if both are polar, but generally speaking polar plastics will not fuse satisfactorily with non-polar plastics. Examples of fusion-compatible plastics which can be used are polypropylene CD-460 produced by E.I. DuPont de Nemours & Co. and ethylene vinyl acetate EVA 3185 produced by Exxon Chemical Co. Nylon and thermoplastic urethanes such as Celanes 1300 Nylon 6/6 and polyurethane Estane 59121 manufactured by B.F. Goodrich Chemical Co. are also compatible. It is of course also possible to substitute thermally or UV crosslinkable rubber forming monomers as disclosed in U.S. Pat. Nos. 5,607,992 or 5,354,532 in place of thermoplastic elastomeric polymers, but for increased chemical bonding and for ease of cleaning the apparatus, thermoplastic polymers are usually preferred.

While the thermoplastic and thermoplastic elastomer compositions used in the present invention are not particularly limited except by functional properties, the elastomer is preferably a thermoplastic elastomer having a Shore A Hardness of from 25 to 98, more preferably from 40 to 80, as defined in the *Handbook of Plastics, Elastomers*, and *Composites*, Charles A. Harper, Second Ed. 1992, McGraw Hill, and particularly, Chapter 7 entitled "Thermoplastic Elastomers", and in *Plastics Engineering Handbook of the Society of the Plastics Industry*, Michael L. Berins, Fifth ed., 1991, pages 72 and 73. Examples of thermoplastic elastomers include thermoplastic polyurethanes, styrenic block copolymers, copolyesters, olefin blends, rubber olefin alloys, neoprene, urea-formaldehyde, polyvinylformaldehyde plastic, polyester resin reacted with aromatic diisocyanates to form a prepolymer which is then reacted with water to form a plastic urethane polymer, phenolformaldehyde resins, and polystyrene, or any other such natural or synthetic material known to those in the art with suitable properties such as resiliency, durability, good extrudability and good appearance. The rigid thermoplastic can be any rigid or semi-rigid polymer, preferably a thermoplastic polymer with a Shore D hardness of from 40 to 74, such as an extrudable polyvinyl chloride, ethylene/methacrylic acid base copolymer, a high density polyethylene copolymer, any of the polyolefins, such as polypropylene and polyethylene, polyethylene terephthalate, polystyrene, acrylonitrilestyrene-butadiene polymer, nylon, acetal polymer, polycarbonate, nitrile resins, polyvinyl alcohol, and polysulfone. See, e.g., U.S. Pat. No. 5,555,913.

Figures 4, 5, 6:
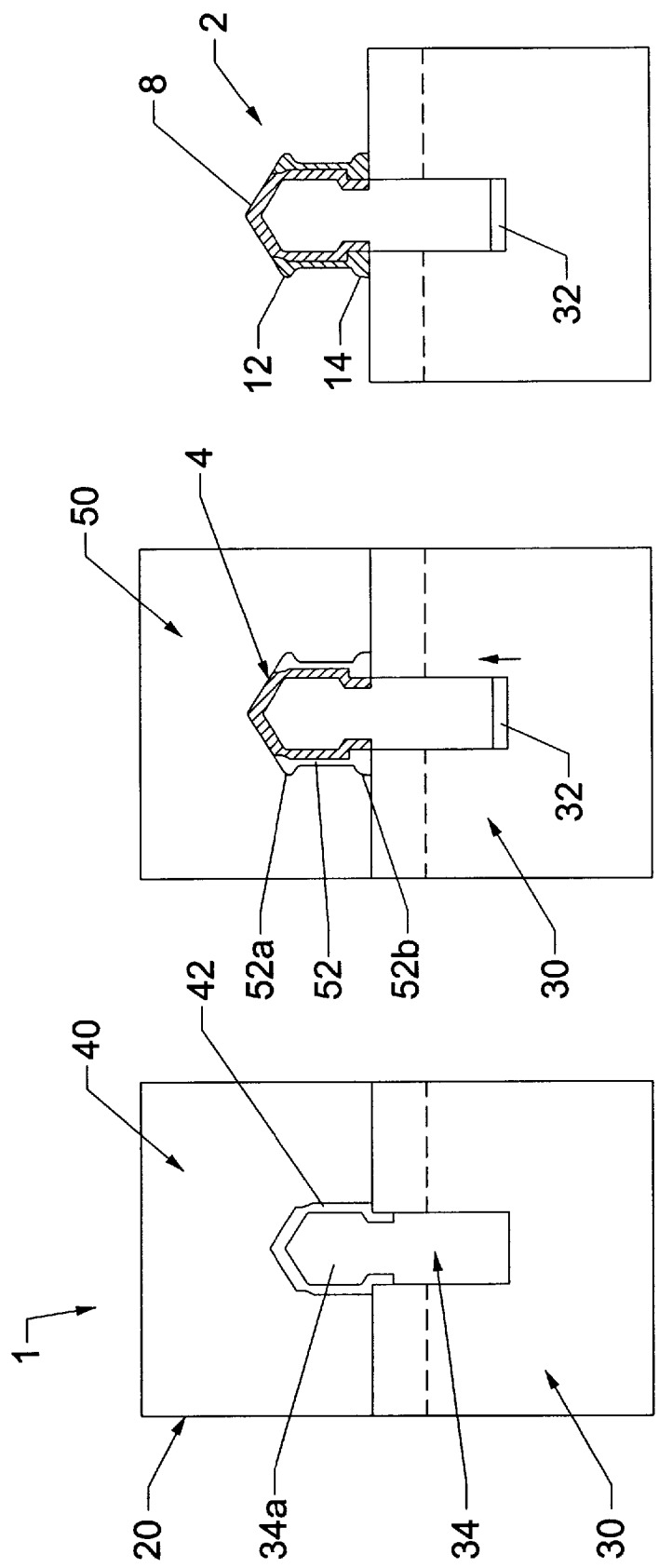
FIG. 4: sets forth a sectional front view of the modular molding apparatus in its "first injection position".
FIG. 5: sets forth a sectional front view of the modular molding apparatus in its "second injection position", after the thermoplastic material has been injected to form the piston inner sheath.
FIG. 6: sets forth a sectional front view of the modular molding apparatus after the thermoplastic rubber material has been injected around the piston inner sheath, thereby forming the composite piston; and after the part of the mold forming the thermoplastic rubber chamber has been removed.

Referring now to FIG. 4, the preferred embodiment of the composite piston 2, described above, is produced in accordance with a preferred mode of practicing the invention by means of a modular mold apparatus 20 that essentially comprises a mold carrier 30. The mold carrier 30 defines a channel 32 (partially observable in FIGS. 5–7), within which is housed a slideable core pin 34. The core pin 34 defines a conical frustum 34A which corresponds to the geometric shape and dimensions of the plunger shaft-end (not shown) to which the composite piston 2 is to be seated. Separably engaged with the mold carrier 30 is a first mold member 40. The first mold member 40 defines a first cavity 42. When the mold carrier 30 is engaged with the first mold member 40, which is the "first injection position", the core pin protrudes into the first cavity 42, as shown in FIG. 4. When the mold carrier 30 is engaged with the first mold member 40, molten thermoplastic is then pressure injected into the first cavity 42 through an injection gate (conventional; not shown). It will be seen that the injected thermoplastic moves through the first mold cavity 42 to fill the volume around the conical frustum 34A of the core pin 34. The injected thermoplastic is permitted to harden. The injected thermoplastic which hardens within the first cavity 42 and around the core pin's conical frustum 34A becomes the inner sheath 4 of the composite piston 2.

Referring now to FIG. 5, the "second injection position" is shown. The first mold member 40 is disengaged and removed from the mold carrier 30. The core pin 34 is extended, as shown in FIG. 5, so that the collar 5 of the inner sheath 4 is outside of the carrier's channel 32. A second mold member 50 is then engaged to the carrier 30 where the first mold member 40 was previously engaged. The second mold member 50 defines a second mold cavity 52. Further, the second cavity 52 defines an upper circular recess 52A and lower circular recess 52B. When the second mold member 50 is engaged with the mold carrier 30, the conical frustum 34A bearing the inner sheath 4 extend into the second mold cavity, as shown in FIG. 5. The second mold cavity 52 is dimensioned to be wider than the previously formed inner sheath 4 and so, once the second mold member 50 is engaged, the inner sheath's conical apex 8 is in sealing contact with the surface of the second mold cavity 52, as shown in FIG. 5 As will be made clear below, this configuration ensures that only the minimum requirement of thermoplastic elastomer is used to form the composite piston.

Molten thermoplastic elastomer is then pressure injected into the second mold cavity 52. It will be seen that the injected thermoplastic moves through the second mold cavity 42 to fill the volume around the previously formed inner sheath 4, which is shrouding the conical frustum 34A. The thermoplastic elastomer is permitted to harden. That elastomer which hardens within the second mold cavity 52 becomes the outer sheath 10 of the composite piston 2, as shown in FIG. 6. Specifically, the elastomer that hardens within the upper circular recess 52A becomes the upper rib seal 12 of the outer sheath 10, and the elastomer that hardens within the lower circular recess 52B becomes the lower rib seal 14 of the outer sheath 10, as shown in FIG. 6. Because there was no space between the inner sheath's conical apex 8 and the surface of the second cavity 52, no elastomer hardens upon the conical apex 8. This is economically ideal, since it is not necessary for the conical apex 8 of the piston 2 to have the elastomeric properties that the upper and lower rib seals 12 and 14 must have for fluid-tightness. Finally, as shown in FIG. 6, the second mold member 50 is disengaged and removed from the mold carrier 30, leaving the finished composite piston 2 seated over the conical frustum 34A.

Figure 7:
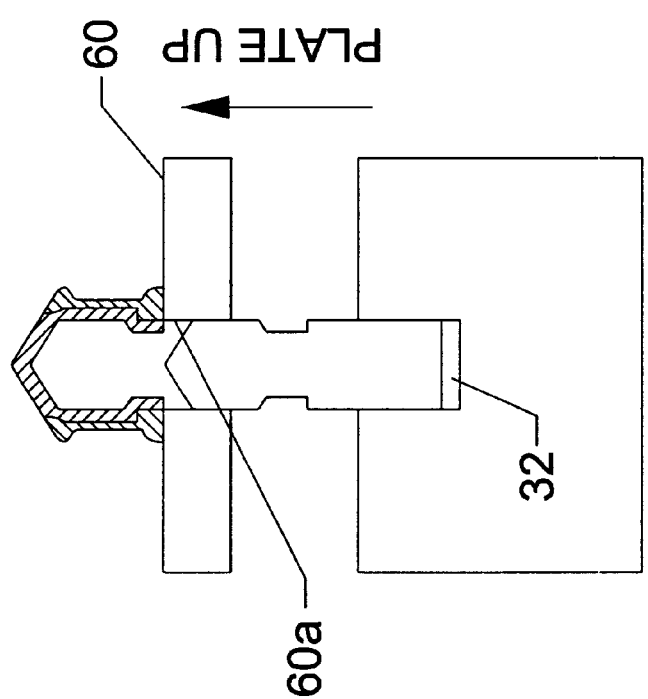
FIG. 7: sets forth a sectional front view of the molding apparatus after the stripper plate has been extended.

Next, to liberate the finished composite piston 2 from the conical frustum 34A, use is made of an extendable stripper plate 60, shown extended in FIG. 7. The stripper plate 60 functions simply to strip the piston 2 from the conical frustum 34A. The stripper plate 60 has an aperture 60A, the diameter of which corresponds to the diameter of the mold carrier's channel 32. An automated means (conventional; not shown) then removes the finished composite piston 2 from the stripper plate 60 so that the piston 2 can be seated on a plunger shaft-end (not shown). The stripper plate 60 must be of a thickness to avoid the creation of flash and deformation of the piston; therefore, the stripper plate 60 should be of a thickness so that the junction of the stripper plate 60 and the mold carrier 30 (shown in phantom in FIGS. 4–6) is preferably half the length of the core pin 34, thereby avoiding contact with any injected molten material.

Figure 8:
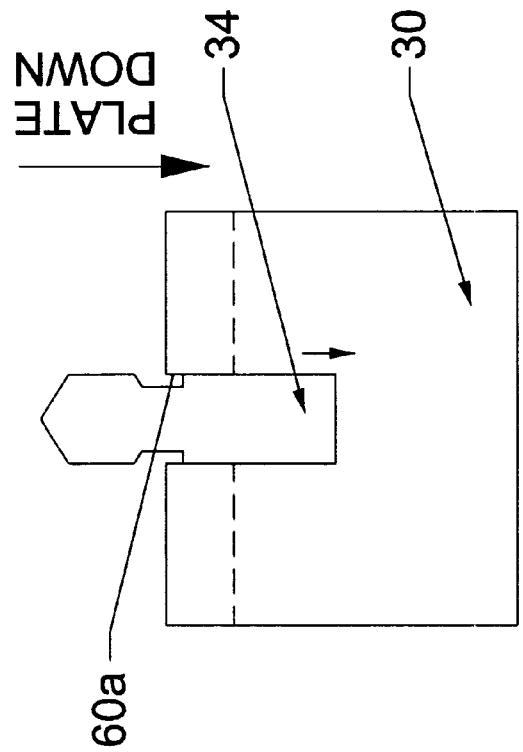
FIG. 8: sets forth a sectional front view of the molding apparatus after the composite piston has been liberated and the stripper plate retracted.

As shown in FIG. 8, the stripper plate 60 then retracts to its original position, just as the core pin 34 returns to its original "first injection position". The piston forming sequence is then ready to start anew with the engagement of the first mold member 40 with the mold carrier 30, as in FIG. 4. As is known in the injection molding industry, many mold cavities may be defined within a single mold apparatus, so as to allow for mass production of the article, which is in this case, a composite piston.

Though not necessarily expressed in the drawings, it has been contemplated by the inventors to round corners and "soften" angles of the composite piston 2 and corresponding parts of the molding apparatus 1 sufficiently to facilitate liberation of the finished piston 2 from the molding apparatus 1, but without thereby compromising either the fusion of the inner sheath 4 with the outer sheath 10 or the interlock of the piston 2 with the plunger shaft (not shown).

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. A piston comprising a rigid inner sheath part and a resilient elastic outer sheath part, wherein said inner sheath part includes an internal surface defining an engagement cavity having a mouth to receive a plunger shaft end, with a mechanical locking collar at said mouth that is capable of reliably securing the plunger shaft in place and an external surface defining a conical apex opposite said mouth and an outer cylindrical surface for receiving said outer sheath; and wherein said outer sheath part is generally cylindrical, is provided to surround only the circumference of said inner sheath outer cylindrical surface, and defines at least one rib seal.

2. A piston as in claim 1, wherein said material for forming said rigid part is a thermoplastic polymer.

3. A piston as in claim 2, wherein said thermoplastic polymer has a Shore D hardness of from 40 to 74.

4. A piston as in claim 3, wherein said thermoplastic polymer is selected from the group consisting of extrudable polyvinyl chloride, ethylene/methacrylic acid base copolymer, high density polyethylene copolymer, polypropylene, polyethylene, polyethylene terephthalate, polystyrene, acrylonitrilestyrene-butadiene polymer, nylon, acetal polymer, polycarbonate, nitrile resins, polyvinyl alcohol, and polysulfone.

5. A piston as in claim 1, wherein said material for forming said elastic part is a thermoplastic rubber.

6. A piston as in claim 5, wherein said thermoplastic rubber is a thermoplastic polypropylene gel infused with a dense matrix of microscopic particles of vulcanized rubber.

7. A piston as in claim 5, wherein said thermoplastic rubber includes a lubricant dispersed therein.

8. A piston as in claim 1, wherein said material for forming said elastic part is a thermoplastic elastomer.

9. A piston as in claim 8, wherein said thermoplastic elastomer includes a lubricant dispersed therein.

10. A piston as in claim 8, wherein said thermoplastic elastomer has a Shore A Hardness of from 25 to 98.

11. A piston as in claim 8, wherein said thermoplastic elastomer is selected from the group consisting of thermoplastic polyurethanes, styrenic block copolymers, copolyesters, olefin blends, rubber olefin alloys, neoprene, urea-formaldehyde, polyvinyl-formaldehyde plastic, polyester resin reacted with aromatic diisocyanates to form a prepolymer which is then reacted with water to form a plastic urethane polymer, phenolformaldehyde resins, and polystyrene.

12. A piston as in claim 1 wherein said piston is adapted for mechanical engagement with a hypodermic syringe plunger shaft, and wherein said piston is adapted for engagement with an internal wall of a cylinder of a hypodermic syringe having a capacity of from 0.5 cc to 500 cc.

13. A piston as in claim 1, wherein said outer sheath part defines two rib seals.

14. A piston comprising a rigid inner sheath part and a resilient elastic outer sheath part, wherein said inner sheath part includes an internal surface defining an engagement cavity having a mouth to receive a plunger shaft end, with a mechanical locking collar at said mouth place, and an external surface defining a conical apex opposite said mouth, and an outer cylindrical surface for receiving said outer sheath; and wherein said outer sheath part encases the exterior of said inner sheath and defines at least one rib seal.

* * * * *